United States Patent [19]

LaBelle et al.

[11] 4,218,534

[45] Aug. 19, 1980

[54] PHAGE DETECTION

[75] Inventors: Gerald G. LaBelle; Glenn E. Staehler, both of Waukesha, Wis.

[73] Assignee: Dairyland Food Laboratories, Inc., Waukesha, Wis.

[21] Appl. No.: 13,001

[22] Filed: Feb. 21, 1979

[51] Int. Cl.² ............................................... C12Q 1/70
[52] U.S. Cl. ........................................ 435/5; 435/34; 435/36; 435/291; 435/296; 435/299; 435/810; 426/41
[58] Field of Search ................. 435/5, 29, 34, 36, 235, 435/291–293, 296, 299–301, 310, 800, 808–810, 885; 426/34, 41, 43, 231

[56] References Cited

U.S. PATENT DOCUMENTS

| Re. 28,276 | 12/1974 | Farr | 435/885 X |
|---|---|---|---|
| 3,041,248 | 1/1962 | Hargrove | 435/885 X |
| 3,117,009 | 1/1964 | Boelter | 435/296 X |
| 3,219,421 | 11/1965 | Schwarz et al. | 435/296 X |
| 3,928,139 | 12/1975 | Dorn | 435/296 X |
| 4,038,143 | 7/1977 | Juni | 435/34 X |
| 4,156,019 | 5/1979 | Kondratenko et al. | 435/885 X |

*Primary Examiner*—R. B. Penland

[57] ABSTRACT

To select a blend of strains not susceptible to the current bacteriophage in the cheesemaking plant the cheesemaker inoculates each of the test tubes in the kit with filtered when obtained from current production. Each tube contains a genetically distinct starter culture strain or a culture blend in a sterile milk medium and contains a dye which will change color in the desired pH range. After incubation for ten hours the cultures resistant to the prevailing phage will exhibit the desired color change and will have developed a firm curd. A starter culture now known to be resistant to the prevailing phage can now be selected. Tests show success closely approaching 100% as opposed to 96% (or less) with the traditional rotation method of selecting culture blends.

17 Claims, 3 Drawing Figures

U.S. Patent    Aug. 19, 1980    4,218,534
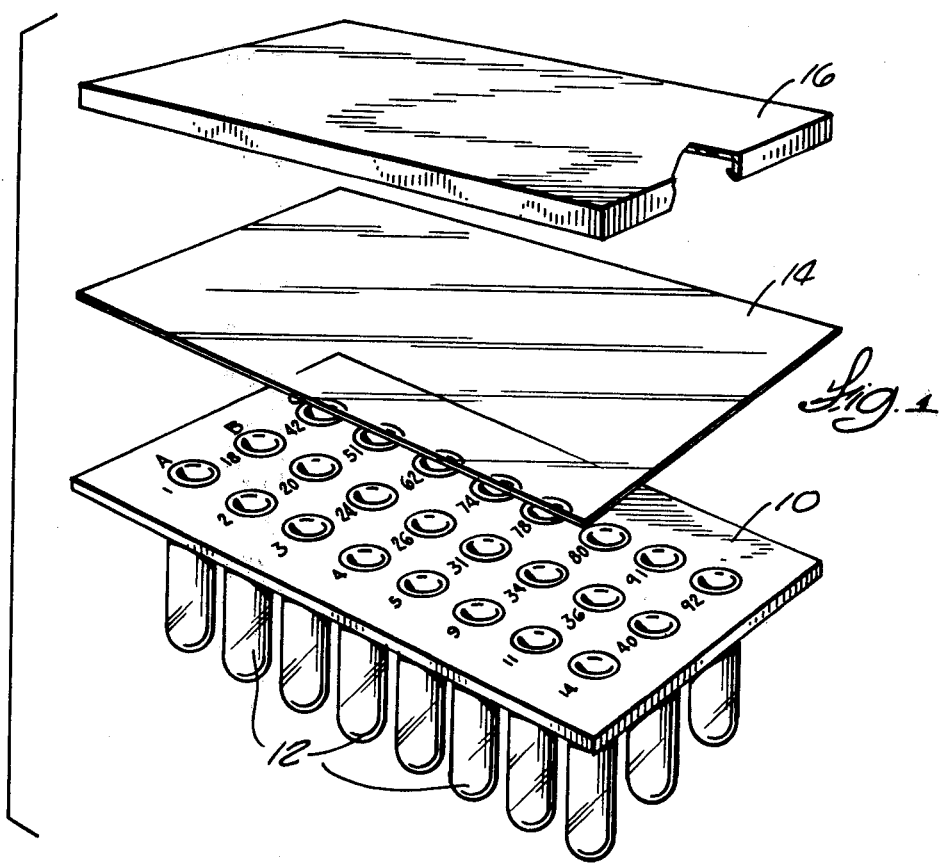
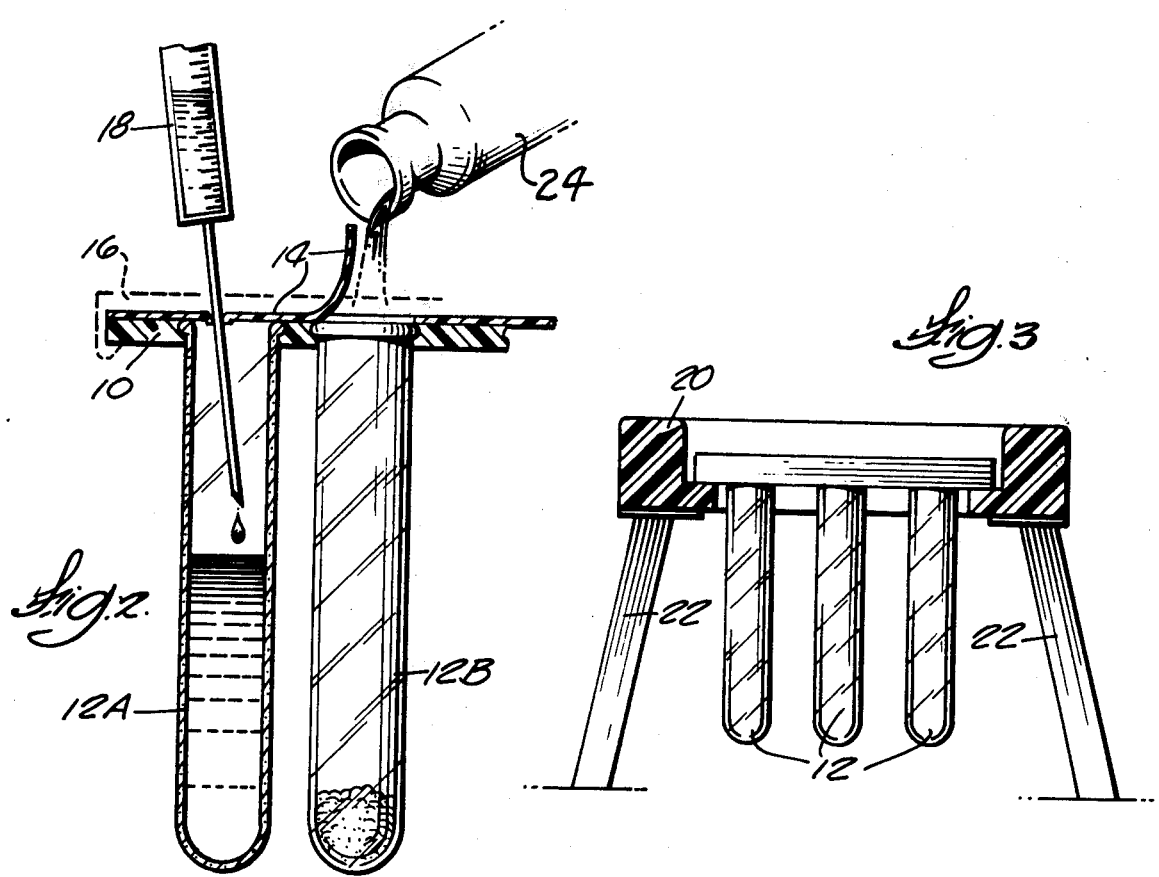

PHAGE DETECTION

BACKGROUND

Production of cheese today is a big business involving the processing of large quantities of milk every day. In order to attain the desired production level it is necessary that the milk clot in a specific period of time. Before clotting can occur there must be lactic acid production. Lactic acid is produced by the action of starter cultures which are lactic acid bacteria which both produce the lactic acid and provide enzyme systems for flavor development during curing. Failure to produce enough lactic acid within the time schedule results in economic loss either through dumping the vat full of milk or by degradation of the cheese quality.

Starter cultures are blends of genetically distinct strains or subclasses or organisms primarily within two classes of lactic acid producing bacteria, including *Streptococcus cremoris* and *Streptococcus lactis*. All culture strains are subject to attack by bacteriophages which are bacterial viruses which can attack bacterial cells, multiply within the bacterial cell and ultimately destroy it. These bacterial viruses are also genetically distinct and this enables the viruses to differentiate between the various strains of starter organisms . . . thus certain viruses will attack only particular strains of *S. cremoris* and *S. lactis*.

Phage is always present. Obviously a starter culture must be resistant to the phage in order to function properly. A given blend which is today resistant cannot be used continuously, however, since the phage continuously undergoes genetic changes and culture strains that were not susceptible can become susceptible as new viruses develop against them. Successful starter culture selection becomes a matter of staying ahead of the change in the phage in the plant. Current methods of guarding against failure involve use of a rotation of blends of strains. The cheesemaker uses a number of different blends on different days. The blends are purchased from suppliers. The relationship between the strains in a blend has usually been determined by experimental methods and by trial and error so the phage produced (built up) against one strain or blend used one day will not attack the blend (or strains therein) used on the following day or the day thereafter. This is called rotation. The basis is trial and error and there is no assurance of success . . . and in practice the rotation system is only about 96% successful. In a large cheese plant 4% is a very significant loss.

A further factor to be considered is the effect of slight loss of starter culture efficiency due to phage attack on one or two of the strains sufficient to lower lactic acid production but still passable (as opposed to dumping the milk). This lowers the cheese quality and the change in acid (pH) could necessitate changes in the processing of the whey (a by-product) causing economic loss.

There are known tests for determining the phage susceptibility. The M17 agar plate method (the *Australian Journal of Dairy Technology*, June 1977, pp 63–64) is used in certain laboratories but is generally regarded as requiring too much skill and experience for the cheese factory. A simpler test involves the use of Bromcresol Purple (BCP) Milk in which the direct acidification of milk is wholly or partially inhibited by phage so that after incubating the resistant (usable) culture has turned yellow while the inhibited (not usable) culture is blue or green. Neither the BCP method nor the M17 agar plate method has been adopted for use in the factory.

SUMMARY OF THE INVENTION

The object of this invention is to allow the cheesemaker to choose his starter culture on the basis of the phage environment in his plant at any particular time.

In carrying out this method the cheesemaker preferably has available to him a multiplicity of genetically distinct strains in each of the three groups of lactic acid producing bacteria which will make up the starter culture. A simple test kit containing each of the strains in his culture bank in a sterile medium and with BCP permits a simple test using whey from current production (the whey will contain the current phage in the plant) to determine which strains in each group are resistant, thus indicating which strains can be used without fear of phage attack. If desired, blends may be used (tested) instead of working with single strains. The final starter culture can be a single strain (as sometimes done in Europe) or a blend (as used in the United States).

We have demonstrated by use of the M17 method that the success of the starter culture can be raised to 100% and we have demonstrated that the BCP method coincides with the M17 results 99.94%. This not only achieves significant direct reduction of losses over the 96% success of the rotation method but achieves significant economics in whey processing. No undergrade cheese was produced when following this method.

The test apparatus is simple and inexpensive. Each culture is in its own "test tube" along with BCP and sterile milk. All recepticles are sealed to maintain sterile conditions. A typical test kit will have 8 "test tubes" in each of three groups of culture strains . . . typically one group will be strains of *S. lactis* and there are 2 groups of *S. cremoris* (8 fast and 8 slow-acting strains as typical in culture blends). Each tube contains sterile milk, BCP and a strain. In use each tube is inoculated with filtered whey from current production and the tubes are then incubated and observed for color change at 6–7 and 16 hours. The strains which have turned yellow can be used safely. The cheesemaker uses any one safe strain from each of the 3 groups to make up a blend which is now known safe. As noted above the same procedure can be applied using different blends in the test tubes. In that event the test will indicate which blends are resistant to the current phage.

Instead of working with frozen (liquid) solution containing the culture, BCP, and sterile medium, the culture and sterile non-fat dried milk (NFDM) can be freeze dried and reconstituted by a solution containing sterile water, BCP and the whey sample. In either event, the method of determining the resistant culture is essentially the same.

DESCRIPTION OF DRAWINGS

FIG. 1 is an exploded perspective view of a test kit.

FIG. 2 is a detail view showing injection of the whey into a test tube and also showing how a solution whey, sterile water and BCP can be added to the freeze dried culture and NFDM.

FIG. 3 shows how the test tray is floated in an incubating bath or supported in a dry incubator.

DESCRIPTION OF PREFERRED EMBODIMENT

The test kit supplied to the cheesemaker is a plastic tray 10 having test tubes 12 pressed into and depending therefrom in 3 rows, A, B, C of 8 tubes each. Row A may be 8 distinct strains of *S. lactis,* Row B may be 8 fast strains of *S. cremoris* and Row C would be 8 slow strains of *S. cremoris.* "Fast" and "slow" terminology is used in the sense reported in the *Dairy Industries* 1972, Vol. 37, Page 73, where a fast strain grows well at 38° C. and slow strains grow slowly above 36°.

The strains are in a BCP milk solution which is prepared by first sterilizing a 10% (V/W) reconstituted non-fat dry milk (NFDM) solution at 121° C., 15 psi for 15 minutes, cooling the solution to room temperature and adding sterile (121° C., 15 psi, 15 min.) 5% Bromcresol Purple solution at the rate of 0.75 cc/1,000 cc of milk solution. Each test tube is filled with 2 ml. of the BCP milk solution and then inoculated with 0.03 cc (1 drop) of a freshly grown (16 hours) milk tube of the appropriate culture strain. A suitable plastic film 14 is then sealed to the top surface of the tray. Suitable coding or indicia for the respective cultures in rows A, B and C corresponding to the cultures inventoried by the cheesemaker can be applied to the tray or film as shown in FIG. 1 in which the various tubes are numbered according to the culture suppliers code. For handling and shipping purposes the rigid plastic cover 16 is snapped over the tray. The finished kit is then frozen for storage but is thawed prior to use.

The BCP-milk-culture color is blue or blue-green. The bromcresol purple is a pH indicator dye which turns from blue color to yellow in response to acid development as the culture strain develops in the presence of the bacteriophage present in a whey sample collected before salting in current cheese production in the plant. The whey sample is filtered and then 0.03 cc (1 drop) is added to each test tube, preferably using a hypodermic syringe 18 as shown in FIG. 2 with respect to tube 12A to puncture the seal film 14 but other methods of inoculating can be used such as pipettes, etc. The tray is now placed in and supported by the foam plastic flotation collar 20 and then placed in an incubation water bath maintained at 30° C. Alternatively the tray can be placed in a dry incubator at 30° C. with the tray and collar supported on legs 22.

After 6 hours incubation (up to 16 hours) the tubes are inspected. The tubes which have formed a firm curd and have turned yellow contain culture strains which are not affected by the phage present and have proper acid production and growth. These strains are suitable for use in making a blend. One strain is selected from those indicated suitable in each row and the 3 strains are mixed. The cultures which remain blue or blue-green after incubation have not produced acid (or curd) properly by reason of the phage attacking the strain. Some tubes may turn yellow-green indicating partial susceptibility to phage attack and while they might be usable the cheesemaker preferably will select from the strains clearly unaffected by the phage. This assures virtually 100% results compared with 96% (at best) obtained with rotation. In a cheese plant processing 2,000,000 pounds of milk per day this means elimination of a 80,000 lb/day loss of milk ( or a gain of 8,000 lbs. of cheese production each day).

Bromcresol purple is the preferred dye but other pH indicator dye are usable, such as methylene blue or resazurin dye. The color changes with BCP are deemed easier to work with. Less than full color change indicates various degrees of susceptibility and for safety sake it is easy to select from the cultures showing full change. The tray and tubes can be made as shown or as a unit and are preferably made of plastic to be a throw away item.

The method can be used in conjunction with freeze dried cultures. In that case the culture strain (blend) would be freeze dried with sterile non-fat dried milk power as in tube 12B in FIG. 2. The filtered whey would be added to a container of sterile water and BCP and the proper amount of that solution would then be added to tube 12B to reconstitute the dried milk and start the test. This approach may be more attractive to the cheesemaker since he does not have to meter out just one drop as in the "wet" approach. The film 14 is simply peeled back to allow addition of the proper amount of the solution of tube 12B and the film is then reclosed to maintain sterile conditions. A dispenser 24 for automatically metering the correct quantity to each tube can be used.

If this method is practiced in conjunction with the blends used by the cheesemaker in the past on a rotation basis, the method can prevent the 4% (or more) loss previously experienced. Thus the cheesemaker can test the next blend normally used in his rotation along with a few other blends. If the test shows his usual "next" to be susceptible to the current phage, he will select a blend which is clearly resistant and avoid the loss.

This method, therefore, can be used with rotation to raise the success rate to 100%. It can be used in conjunction with genetically distinct strains to permit the widest choice of blends and complete orchestration of the culture art. And it can be used to select a single strain with assured results for those preferring that approach.

We claim:

1. A method for selecting a cheese starter culture resistant to the bacteriophage currently present in a cheese factory comprising the steps of,
   preparing a multiplicity of test samples of different strains or blends of starter cultures differing one from another and corresponding to the cultures available to the cheesemaker, each sample being in a sterile medium to which has been added a pH indicator dye which changes color in response to acid production in the curd forming process,
   adding to each test sample an inoculant containing phage then present in the cheese factory,
   incubating the test samples for a period of time sufficient for acid production and curd formation,
   determining which of the incubated test samples has changed color indicative of acid production and has developed satisfactory curd to thereby indicate resistance to the phage present in the inoculant,
   and selecting for use as a starter culture in production of cheese at least one phage resistant culture from those determined satisfactory in the preceding step.

2. The method of claim 1 in which the inoculant is whey taken from current cheese production.

3. The method of claim 2 in which the dye is a pH indicator dye, the sterile medium is reconstituted non-fat milk, and the test culture includes both fast and slow strains of *S. cremoris.*

4. The method of claim 3 in which the selected starter culture contains more than one culture strain.

5. The method of claim 4 in which the starter cultures making up the test samples are genetically distinct cultures of *S. lactis* and *S. cremoris.*

6. The method of claim 5 in which the selected starter culture is a blend of said cultures.

7. The method of claim 6 in which the test samples include both fast and slow strains of *S. cremoris* and the selected culture includes both fast and slow strains.

8. The method of claim 3 in which each test sample includes the culture in a sterile milk medium containing said dye and the whey is added thereto.

9. The method of claim 3 in which each test sample contains freeze dried non-fat milk and the culture, the milk being reconstituted by addition of sterile water, the whey being added to the test sample separately or in combination with the sterile water.

10. Apparatus for testing different strains or blends of cheese starter cultures for resistance to the bacteriophage present in a cheese factory, comprising tray means having a multiplicity of sealed test tubes,
    each test tube containing a dye, a culture medium and a culture different from the other cultures,
    each sealed test tube having means for introduction of an inoculant,
    said dye being a pH indicator dye which changes color in response to lactic acid development by reason of culture growth in the medium after the medium has been inoculated with a liquid inoculant solution containing phage present in the factory and then incubated,
    lack of color change in a culture indicating phage susceptibility of the culture and a desired color change indicating phage resistance of the culture, whereby a usable culture may be selected from those exhibiting the desired color change.

11. Apparatus according to claim 10 in which the culture medium is sterile non-fat dried milk.

12. Apparatus according to claim 11 in which the medium and the test culture are freeze dried and are reconstituted by later addition of sterile water.

13. Apparatus according to claim 10 in which there are a multiplicity of test tubes containing genetically distinct cultures strains of *S. lactis* and a multiplicity of test tubes containing genetically distinct culture strains of *S. cremoris*.

14. Apparatus according to claim 13 in which there are a multiplicity of fast *S. cremoris* culture strains and a multiplicity of slow *S. cremoris* culture strains.

15. Apparatus according to claim 14 in which the *S. lactis* cultures are separately grouped in the tray means as are the fast *S. cremoris* cultures and the slow *S. cremoris* cultures.

16. Apparatus according to claim 15 including indicia associated with each test tube serving to identify the respective cultures adequately for the user to select corresponding cultures from his culture inventory.

17. Apparatus according to claim 15 including flotation means for supporting the tray means in an incubating bath with the test tubes in the bath.

* * * * *

UNITED STATES PATENT AND TRADEMARK OFFICE
CERTIFICATE OF CORRECTION

PATENT NO. : 4,218,534
DATED : August 19, 1980
INVENTOR(S) : Gerald G. LaBelle et al It is certified that error appears in the above-identified patent and that said Letters Patent are hereby corrected as shown below:

In the Abstract, line 4, change "when" to --whey--.

Signed and Sealed this

Thirteenth Day of January 1981

[SEAL]

Attest:

SIDNEY A. DIAMOND

*Attesting Officer*    *Commissioner of Patents and Trademarks*